Figure 1:
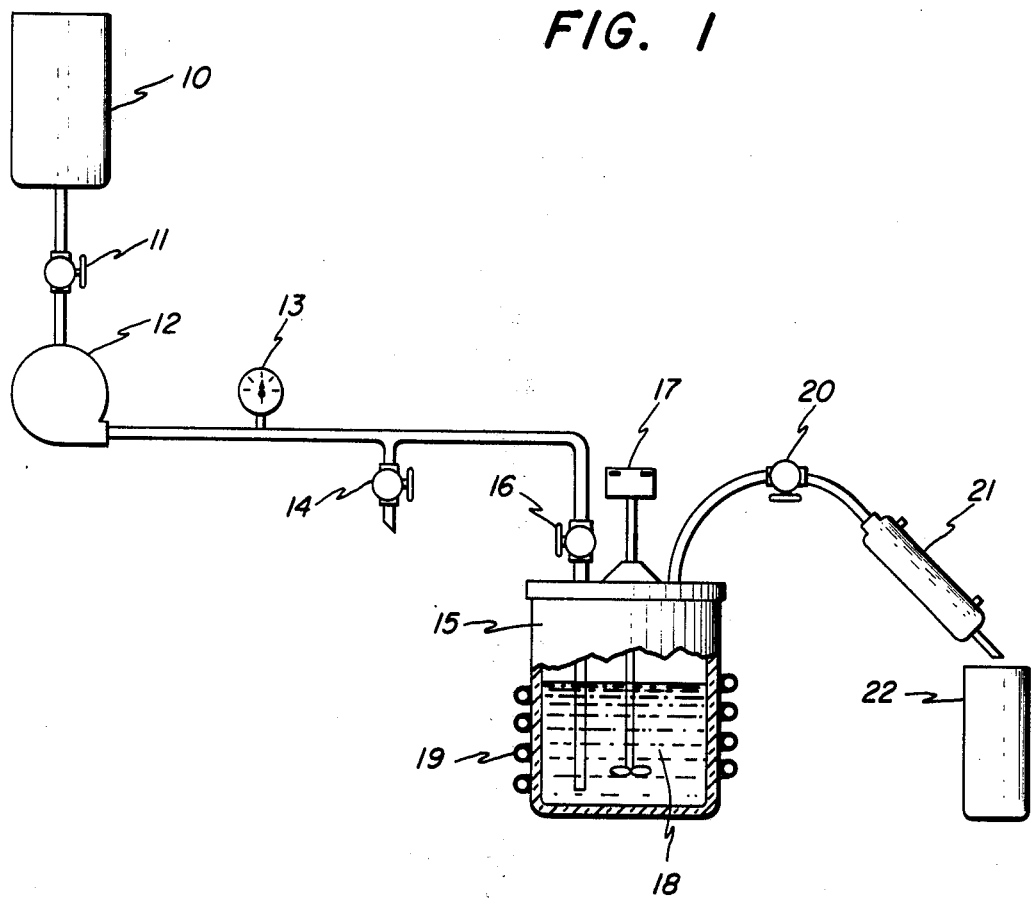
Figure 2:
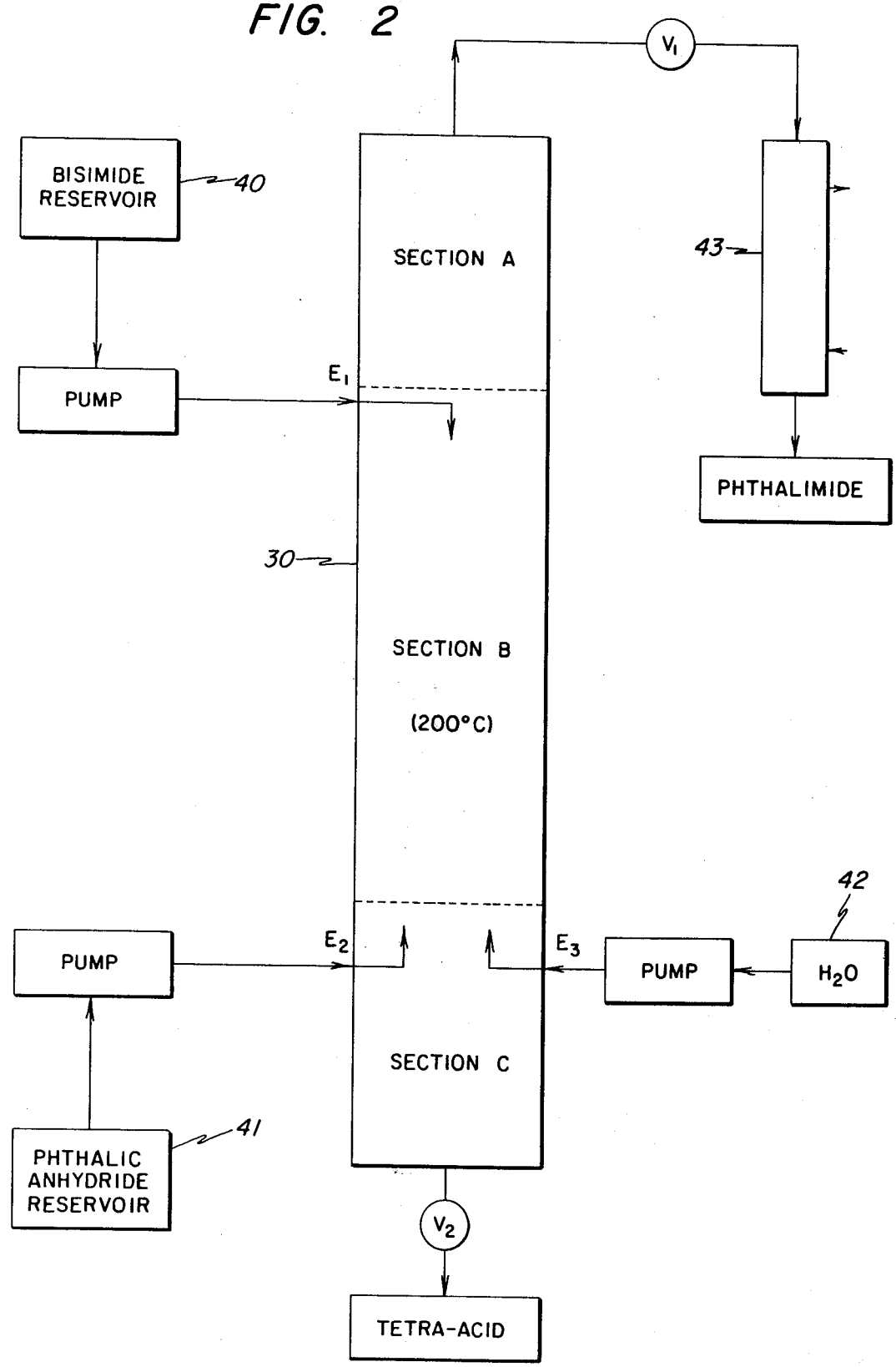

United States Patent [19]

Webb

[11] 4,116,980

[45] Sep. 26, 1978

[54] METHOD FOR MAKING AROMATIC BIS (ETHER PHTHALIC ACID) OR AROMATIC BIS (ETHER ANHYDRIDE)S

[75] Inventor: Jimmy L. Webb, Ballston Lake, N.Y.

[73] Assignee: General Electric Company, Schenectady, N.Y.

[21] Appl. No.: 729,127

[22] Filed: Oct. 4, 1976

[51] Int. Cl.$^2$ .......................................... C07D 307/89
[52] U.S. Cl. .............................. 260/346.3; 260/326 R; 260/326 HL; 562/473; 562/469
[58] Field of Search ............ 260/346.3, 520 E, 326 R, 260/326 HL

[56] References Cited

U.S. PATENT DOCUMENTS

| | | | |
|---|---|---|---|
| 3,879,428 | 4/1975 | Heath et al. | 260/346.3 |
| 3,933,852 | 1/1976 | Cook et al. | 260/326 N |
| 3,957,862 | 5/1976 | Heath et al. | 260/520 E |
| 4,062,648 | 1/1977 | Puskas et al. | 260/346.3 |

OTHER PUBLICATIONS

Groggins, Unit Processes in Organic Synthesis, McGraw-Hill (New York) 1952, pp. 609 to 611, 619 and 620.

Michman et al., J. Chem. Soc. (c), 1971, pp. 3856 to 3859.

*Primary Examiner*—Richard L. Raymond
*Attorney, Agent, or Firm*—William A. Teoli; Joseph T. Cohen; Charles T. Watts

[57] ABSTRACT

A method is provided for converting aromatic bis(ether N-organo substituted phthalimide) to aromatic bis(ether anhydride) by heating an aqueous mixture under pressure, of aromatic bis (ether N-organo substituted phthalimide) and phthalic anhydride, or phthalic acid. An exchange is effected between phthalic anhydride or phthalic acid and the aromatic bis(ether N-organo substituted phthalimide) to produce a liquid phase mixture of aromatic bis(ether phthalic acid) and an aqueous vapor phase mixture of N-organo substituted phthalimide. The N-organo substituted phthalimide is selectively removed from the liquid phase mixture by venting the vapor phase therefrom.

12 Claims, 2 Drawing Figures

METHOD FOR MAKING AROMATIC BIS (ETHER PHTHALIC ACID) OR AROMATIC BIS (ETHER ANHYDRIDE)S

The present invention relates to a method for making aromatic bis(ether phthalic acid) or aromatic bis(ether phthalic anhydride) by effecting an exchange between an aromatic bis(ether phthalimide) and phthalic acid or phthalic anhydride.

Prior to the present invention, as shown by Heath et al, U.S. Pat. Nos. 3,879,428 and 3,957,862, assigned to the same assignee as the present invention, aromatic bis(ether anhydride) of the formula,

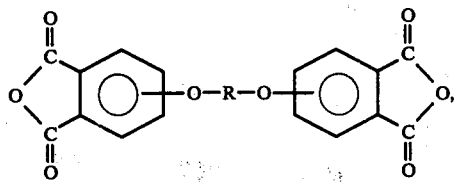 (1)

was made by a multistep procedure involving the base hydrolysis of an aromatic bis(ether N-organo substituted phthalimide) of the formula,

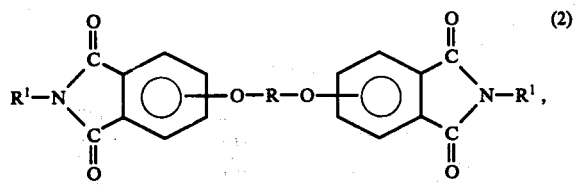 (2)

where R and $R^1$ are defined below, to produce a tetra-acid salt which was thereafter acidified to the tetra-acid followed by the dehydration of the tetra-acid to produce the aromatic bis(ether anhydride) of formula (1).

Although the procedure of Heath et al provides a valuable route to both the aromatic bis(ether phthalic acid) and aromatic bis(ether anhydride, it requires the base hydrolysis of the aromatic bis(ether N-organo substituted phthalimide) of formula (2), or "bisimide", and the conversion of the resulting salt to the tetra-acid, followed by the dehydration of the tetra-acid. In addition to requiring a variety of steps to convert the bisimide to a bisanhydride, inorganic salts can be generated causing diposal problems. Efforts are, therefore, being directed to providing a more simplified procedure for making the aromatic bis(ether anhydride) of formula (1) or "bisanhydride" or the tetra-acid precursor.

As shown in copending application RD-8590 of Ronald L. Markezich and Tohru Takekoshi, filed concurrently herewith and assigned to the same assignee as the present invention, an imide-anhydride exchange reaction is provided resulting in the production of organic polycarboxylic acids, anhydrides thereof, or organic imides. For example, in particular instances a bisimide, such as 2,2-bis[4-(3,4-dicarboxyphenoxy)phenyl]propane bis-N-methylimide is heated with phthalic anhydride in the presence of water to effect an exchange between the aforementioned bisimide and phthalic anhydride to produce the corresponding tetra-acid or anhydride thereof.

Although the Markezich et al method eliminates many of the disadvantages of the prior art, such as permitting the ready conversion of N-alkyl substituted bisimides, the direct production of cyclic anhydrides, forming inorganic salts, or the requirement of a multistep procedure, Markezich et al is essentially a batch method. The recovery of the tetra-acid or bisanhydride at a satisfactory yield requires several heating and stripping cycles. It is also difficult to achieve substantial conversion of the bisimide to the tetra-acid or the bisanhydride without resort to the recycling of excessive amounts of phthalic acid or phthalic anhydride. Based on the nature of the exchange between the bisimide and the phthalic acid or phthalic anhydride, optimum conversion cannot be realized unless the N-organo phthalimide, which is also formed in the reaction, is separated from the mixture.

The present invention is based on the discovery that optimum conversion of the bisimide to the tetra-acid or dianhydride thereof can be achieved based on an imide-anhydride exchange in the presence of water, as shown by the following, $$A + B \rightleftarrows A' + B',$$

where A and A' are imides and B and B' are anhydrides, if the A' imide is selectively removed from the reaction during the exchange. For example, in the above equation, A can be a bisimide, B can be phthalic acid, B' can be a bisanhydride or tetra-acid and A' can be an N-organo phthalimide.

It has been found that the aforementioned results can be achieved by venting a portion of the vapor phase of the reaction mixture consisting of a liquid phase and a vapor phase during the exchange. A surprising result is that the vapor phase consisting essentially of water and N-organo phthalimide contains so little phthalic acid, such as less than 5% by weight of vaporous mixture, in view of the similarity in boiling points of these aromatic compounds. Accordingly, by continuously venting the vapor phase from the reaction mixture during the exchange, the reaction is driven to the right. It is, therefore, possible to convert the starting bisimide to the corresponding tetra-acid or bisanhydride without either shutting down the reactor or recycling excessive amounts of phthalic acid.

There is provided by the invention, a method for making aromatic bis(ether phthalic acid) of the formula,

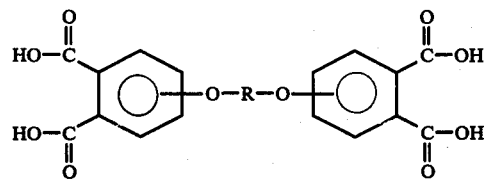

which comprises,
(A) heating at a temperature of 100°–300° C., a mixture comprising by weight,
(i) aromatic bis(ether phthalimide) of formula (2),
(ii) 0.01 to 100 parts of water, per part of (i),
(iii) 0.3 to 20 parts of phthalic anhydride or phthalic acid per part of (i),
to produce a liquid phase-vapor phase reaction mixture, comprising aromatic bis(ether phthalic acid) and phthalic acid in the liquid phase, and an N-organo substituted phthalimide of the formula,

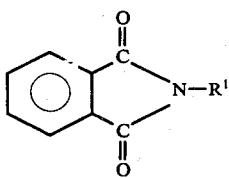

in the vapor phase, (B) venting the vapor phase from the reaction mixture of (A), and (C) recovering the aromatic bis(ether phthalic acid) from the resulting mixture of (B), where R is a divalent aromatic radical having from 6-30 carbon atoms and $R^1$ is a monovalent organo radical selected from the class consisting of $C_{(1-8)}$ alkyl radicals, and organic radicals having from 6-20 carbon atoms, selected from the class consisting of aromatic hydrocarbon radicals and halogenated derivatives thereof.

Radicals included by R are more particularly

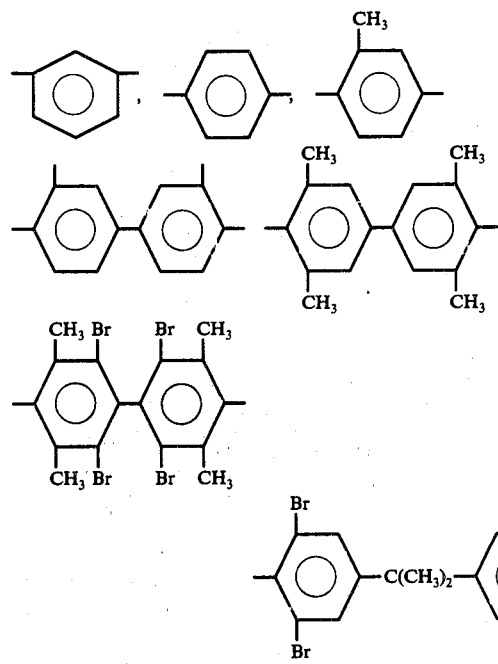

and (b) divalent organic radicals of the general formula

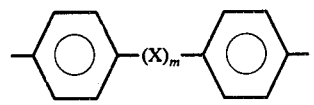

where X is a member selected from the class consisting of divalent radicals of the formulas, $-C_yH_{2y}$,

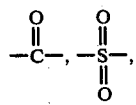

—O—, and —S—, where m is 0 or 1, y is a whole number from 1 to 5.

Radicals included by $R^1$ are, for example, phenyl, tolyl, xylyl, naphthyl, chlorophenyl, bromonaphthyl, etc., and alkyl radicals, such as methyl, ethyl, etc.

This bisimides of formula (2) and a method for making them, are more particularly shown in the aforementioned patent 3,879,428, Heath et al, which is based on the initial formation of an N-organo substituted phthalimide of the formula,

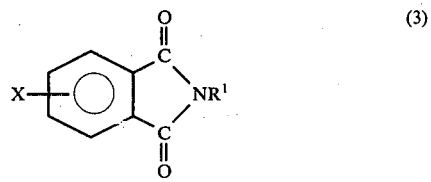

where X is a radical selected from the class consisting of nitro, halo, fluoro, bromo, etc., $R^1$ is as previously defined. The phthalimide of formula (3) can be formed by effecting reaction between a substituted phthalic anhydride and an organic amine, such as aniline, toluidine, etc., methyl amine, ethyl amine, etc.

Included by the phthalimides of formula (3) are, for example, N-methyl-4-nitro-phthalimide, N-phenyl-3-nitrophthalimide, N-phenyl-4-(nitrophthalimide), N-methyl-3-nitrophthalimide, N-butyl-4-nitrophthalimide, etc. As further shown in U.S. Pat. No. 3,879,428, the aromatic bis(ether phthalimide)s of formula (2) can be made by effecting reaction between phthalimides of formula (3) and alkali diphenoxide of the formula, $$M-O-R-O-M \qquad (4)$$

where R is as previously defined, and M is a metal ion of an alkalide metal selected from the class consisting of sodium, potassium, lithium, etc.

Included by the alkali diphenoxides of formula (4), are sodium and potassium salts of the following dihydric phenols 2,2-bis(2-hydroxyphenyl)propane;
2,4'-dihydroxydiphenylmethane;
bis-(2-hydroxyphenyl)methane;
2,2-bis-(4-hydroxyphenyl)propane hereinafter identified as "Bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfoxide;
4,4'-dihydroxydiphenyl sulfide;
hydroquinone;
resorcinol;
3,4'-dihydroxydiphenylmethane;
3,4'-dihydroxybenzophenone;
4,4'-dihydroxybenzophenone; and
4,4'-dihydroxydiphenylether.

A More complete understanding of the practice of the method of the present invention can be obtained by reference to the drawings.

FIG. I is a schematic diagram showing how the invention can be practiced in a batchwise manner using an autoclave as the reactor.

FIG. II shows how the invention can be practiced in a continuous manner where the reactor is a distillation column.

There is shown, more particularly, in FIG. I at 10 a reservoir for water or an aqueous catalyst solution. An aqueous organic carboxylic acid solution can be used having a concentration of from 0.01% to 80% by weight of acid, based on the weight of water. Some of the organic carboxylic acids which can be used are, for example, acetic acid, propionic acid, benzoic acid, isophthalic acid, terephthalic acid, etc. In addition to organic carboxylic acids, other acids can be used, such as hydrochloric, sulfuric, benzene sulfonic acid, etc. Aqueous solutions of organic amines, such as, trimethyl amine, triethyl amine, tripropyl amine, triethylene diamine (DABCO), etc., also can be used.

The reservoir is also equipped with a valve at 11. There is shown at 12, a metering pump which is capable of delivering the catalyst mixture at a controlled rate into the reactor which can be operated at super atmospheric pressures, e.g., from 200 psi or below up to about 1000 psi or more gauge pressure. A pressure gauge is shown at 13 and a valve for sampling the aqueous feed is shown at 14.

A high pressure reactor, such as an autoclave or a Parr bomb is shown at 15 having a valve at 16 for introducing the aqueous feed; there is also shown a stirrer at 17, a dip tube at 18 and a heating coil at 19. In the reactor, there is charged a mixture of bisimide and phthalic anhydride or phthalic acid. A bleed-off valve is shown at 20 for separating vaporous material from the reactor and a condenser at 21 for recovering the vaporous reaction product, such as water, the N-organo phthalimide, etc.

In FIG. II, there is shown a distillation column at 30. The distillation column is divided into 3 sections, section A, section B and section C. A heating coil not shown is employed to maintain the distillation column at a temperature of from 100° C. to 300° C. during operation.

There is also shown in FIG. II a reservoir at 40, which maintains a source of heated bisimide at a temperature sufficient to melt it. There also is shown a pump which is capable of delivering the molten bisimide into the distillation column at $E_1$. At 41, there is shown a reservoir for phthalic anhydride which can be pumped into the distillation column in a molten state at $E_2$. A source of water at 42 can be pumped into the distillation column at $E_3$.

Reaction occurs between the bisimide and the phthalic anhydride in section B of the distillation column as a result of the contact between the molten bisimide as it trickles down the column and the phthalic anhydride as it is distilled up the column. Simultaneously, water, or an aqueous catalyst mixture is constantly being pumped into the resulting mixture at $E_3$. The tetra-acid reaction product, or bisanhydride thereof, forms continuously as a melt in section C. $V_2$ shows bisanhydride can be at least intermittently drawn off in a regulated manner.

At the upper end of the distillation column in section A, the N-organo phthalimide and water, along with other volatiles, is vented from the distillation column by means of $V_1$, a flow regulation valve. The vented reaction product is then led into a condenser at 43 and a mixture of the N-organo phthalimide and water is recovered in receiver-A as shown.

Those skilled in the art would know that the above-described method for making the bisanhydride in a continuous manner is based on the ability to selectively remove the N-organo phthalimide from the reaction mixture even while the exchange between the bisimide and the phthalic anhydride is taking place. Direct nitration of the separated N-organo phthalimide in accordance with Cook et al U.S. Pat. No. 3,933,852, assigned to the same assignee as the present invention results in the production of nitro phthalimide of formula (3). The advantages achieved by combining the exchange reaction of Markezich et al as discussed above with the discovery of the present invention, namely, the selective removal of the N-organo phthalimide from the exchange reaction mixture, provides for the production of the bisanhydride in essentially a three step reaction, namely, the nitration of the N-organo phthalimide, the displacement of the nitro radicals with a diphenoxide as shown by formula (4) to produce the bisimide, followed by the aforementioned exchange to regenerate the N-organo phthalimide. In the original five step reaction it was necessary to aminate the phthalic anhydride, nitrate the resulting N-organo phthalimide, form the bisimide by the aforementioned displacement reaction using a diphenoxide, hydrolyze the bisimide and thereafter cyclize the hydrolysis product.

In order that those skilled in the art will be better able to practice the invention, the following examples are given by way of illustration and not by way of limitation. All parts are by weight.

EXAMPLE 1

In accordance with FIG. 1, an autoclave was charged with 20 parts of 2,2-bis[4-(3,4-dicarboxyphenoxy)phenyl]propane bis-N-methyl imide, 22.75 parts of phthalic anhydride and 250 parts of water. The autoclave was sealed and heated with stirring resulting in an autogenous pressure of about 200 psi. After the mixture had been heated for 1 hour, a vent valve was opened and the vaporous mixture was passed through a condensor at a rate of about 2–8 parts per minute. A solid precipitated from the aqueous distillate and was recovered by filtration. The solid was N-methyl phthalimide. The aqueous condensate was recycled to the mixture by means of a high pressure pump.

After the mixture was heated for 14.2 hours, the mixture was allowed to cool to ambient temperatures. An additional 20 parts of phthalic anhydride was added to the autoclave. After the above procedure was repeated, another 10 parts of phthalic anhydride was added to the mixture about 16.5 hours later. After 2.5 hours of additional heating, there was recovered a total of 8.6 parts of N-methyl phthalimide. The mixture was allowed to cool to room temperatures. The contents of the autoclave were then distilled at 250° C. at 60 mm. There was obtained a 99% yield of 2,2-bis[4-(3,4-dicarboxyphenoxy)phenyl]propane dianhydride.

EXAMPLE 2

In accordance with the procedure of Example 1, there is charged to an autoclave, 27 parts of 2,2-bis[4-(3,4-dicarboxyphenoxy)phenyl]propane bis-N-methyl imide, 29 parts of phthalic anhydride, 200 parts of water and 200 parts of propionic acid. The autoclave is sealed and heated to 200° C. with stirring. After the mixture is heated for 1 hour, a vent valve is opened. The mixture is allowed to escape and passed into a condenser at a rate which results in the production of 10-15 parts per minute of condensate, consisting of water, propionic acid and N-methyl phthalimide and phthalic acid in about a 20/1 mol ratio. The solids are separated and the filtrate is returned to the reservoir and pumped into the autoclave at a rate which is approximately equivalent to the rate of removal of volatiles from the reaction mixture. This process is continued for 12 hours. The autoclave is allowed to cool to ambient temperatures. The cool autoclave is found to provide a yield of 175 parts of a liquid from which a 99% yield of 2,2-bis[4-(3,4-dicarboxyphenoxy)phenyl]propane is obtained in the same manner as in Example 1. Its identity is confirmed by its method of preparation and its infrared spectrum.

Those skilled in the art would know that the above example utilizing propionic acid as an acid catalyst in the above-identified exchange reaction significantly enhances the rate of exchange. A reaction providing a 99% yield of the tetra-acid required 50 hours, while only 12 hours was required to obtain an equivalent yield of the tetra-acid utilizing propionic acid as a catalyst employing the same recovery procedure.

EXAMPLE 3

The process of Example 2 is repeated except that there is used 32 parts of 2,2-bis[4-(3,4-dicarboxyphenoxy)phenyl] bis-N-methyl imide, 17 parts of phthalic anhydride, 300 parts of water and 56 parts of tri-N-butyl amine. The removal of N-methyl phthalimide is effected by using the vent valve as shown in FIG. 1 and as previously described. A mixture of water and tributyl amine containing a trace amount of phthalic acid is returned to the autoclave at a rate substantially equivalent to the venting rate. A quantitative yield of the 2,2-bis[4-(3,4-dicarboxyphenoxy)phenyl]propane is recovered after a 10-20 hour heating period.

Again, as indicated in Example 2, those skilled in the art would know that the tri-N-butyl amine catalyst substantially accelerates the rate of exchange over that shown in Example 1, where no catalyst is employed.

EXAMPLE 4

As shown in FIG. II, a bubble cap distillation column is heated in section C at a temperature sufficient to maintain a temperature of above 200° C. throughout section B. Molten 2,2-bis[4-(3,4-dicarboxyphenoxy)-phenyl]propane bis-N-methyl imide is pumped into the distillation column at $E_1$. Simultaneously molten phthalic anhydride is pumped into the distillation column at $E_2$. In addition, steam is introduced into the distillation column at $E_3$. The vaporous mixture is vented via valve $V_1$ through a condenser as shown, resulting in the production of a mixture of N-methyl phthalimide, phthalic acid and water. Molten 2,2-bis[4-(3,4-dicarboxyphenoxy)phenyl]propane-bis-anhydride is intermittently collected in a receiver as shown.

In accordance with the teaching of Newell Cook et al in the above described patent, the N-methyl phthalimide is nitrated by contacting the N-methyl phthalimide dissolved in concentrated sulfuric acid with concentrated nitric acid at a temperature of from about 60° C. to 80° C. and thereafter extracting nitrated N-methyl phthalimide with methylene chloride. A displacement is thereafter effected between the nitrated N-methyl phthalimide and the disodium salt of bisphenol-A, as shown in Heath et al U.S. Pat. No. 3,879,428, assigned to the same assignee as the present invention. The resulting bisimide is then recycled into the bisimide reservoir to be melted and reintroduced into the bubble cap reactor.

Although the above examples are limited to only a few of the very many variables which can be used in the practice of the method of the present invention, it should be understood that the present invention is directed to a much broader procedure for making tetra-acid and bisanhydride, as previously defined, in a continuous manner or in a semicontinuous manner, as shown in FIG. I. Many of the parameters which are not shown in the examples are shown in the description preceding these examples.

What I claim as new and desire to secure by Letters Patent of the United States is:

1. A method for making aromatic bis(ether phthalic acid) of the formula,

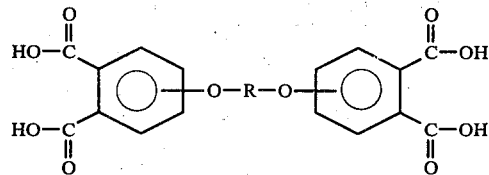

which comprises,
(A) heating at a temperature of 100°-300° C., a mixture comprising by weight
  (i) aromatic bis(ether phthalimide) of the formula,

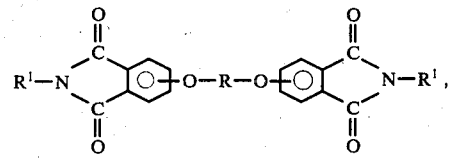

(ii) 0.01 to 100 parts of water, per part of (i)
  (iii) 0.3 to 20 parts of phthalic anhydride or phthalic acid per part of (i),
to produce a liquid phase-vapor phase reaction mixture, comprising aromatic bis(ether phthalic acid) and phthalic acid in the liquid phase, and an N-organo substituted phthalimide of the formula,

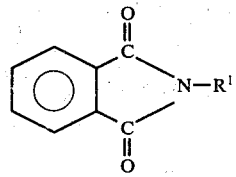

in the vapor phase,
(B) venting the vapor phase from the reaction mixture of (A), and
(C) recovering the aromatic bis(ether phthalic acid) from the resulting mixture of (B),
where R is a divalent aromatic radical having from 6-30 carbon atoms and $R^1$ is a monovalent organo radical selected from the class consisting of $C_{(1-8)}$ alkyl radicals, and organic radicals having from 6-20 carbon atoms, selected from the class consisting of aromatic hydrocarbon radicals and halogenated derivatives thereof.

2. A continuous method for making an aromatic bis(-dicarbonyl) compound, selected from the class consisting of a tetra-acid of the formula,

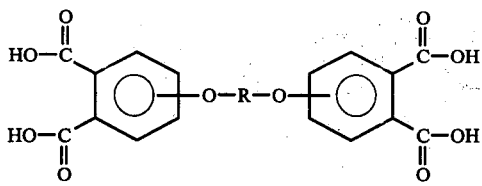

and a bisanhydride of the formula,

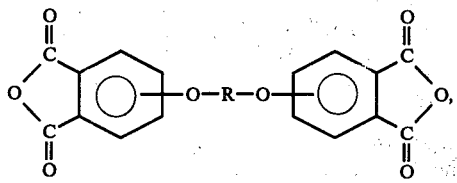

which comprises,
(A) heating at a temperature of 100° C.–300° C., a mixture comprising by weight
(i) aromatic bis(ether phthalimide) of the formula,

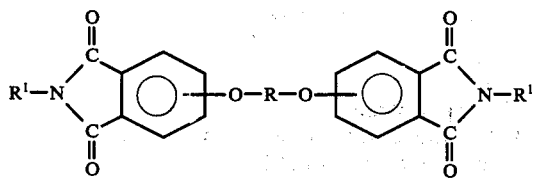

(ii) 0.01 to 100 parts of water, per part of (i)
(iii) 0.3 to 20 parts of phthalic anhydride or phthalic acid per part of (i), to produce a multiphase reaction mixture comprising aromatic bis(ether phthalic) acid and phthalic acid in a liquid phase, and comprising an N-organo substituted phthalimide of the formula,

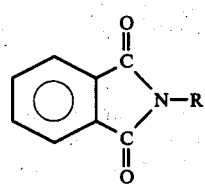

in the vapor phase,
(B) venting the vapor phase from the reaction mixture of (A) to provide for the selective removal of the N-organo substituted phthalimide,
(C) introducing make-up phthalic acid or phthalic anhydride, and bis(ether phthalimide) into the resulting mixture of (A),
(D) introducing water into the resulting mixture of (A), and
(E) recovering the aromatic bis(dicarbonyl) compound from the resulting mixture of (A), where R is a divalent aromatic radical having from 6–30 carbon atoms, $R^1$ is a monovalent organo radical selected from the class consisting of $C_{(1-8)}$ alkyl radicals and organic radicals having from 6–20 carbon atoms, selected from the class consisting of aromatic hydrocarbon radicals and halogenated derivatives thereof.

3. A continuous method for making aromatic bis(dicarbonyl) compound selected from the class consisting of a tetra-acid of the formula,

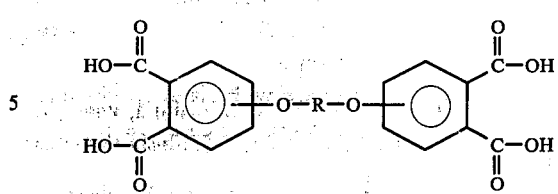

and a bisanhydride of the formula,

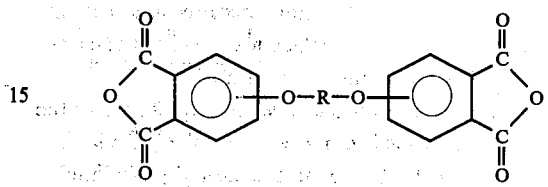

which comprises,
(A) heating at a temperature of 100°–300° C., a mixture comprising by weight
(i) aromatic bis(ether phthalimide) of the formula

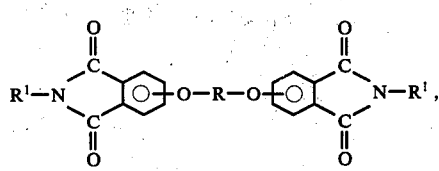

(ii) 0.01 to 100 parts of water, per part of (i)
(iii) 0.3 to 20 parts of phthalic anhydride of phthalic acid per part of (i), to produce a multiphase reaction mixture comprising aromatic bis(ether phthalic) acid and phthalic acid in a liquid phase, and comprising an N-organo substituted phthalimide of the formula,

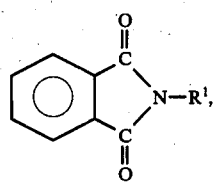

in the vapor phase,
(B) continuously venting the vapor phase from the reaction mixture of (A) to provide for the selective removal of the N-organo-substituted phthalimide,
(C) continuously introducing make-up water into the resulting mixture of (A)
(D) continuously introducing make-up phthalic anhydride or phthalic acid into the mixture of (A), and
(E) at least intermittently recovering bis(dicarbonyl) compound from the resulting mixture of (A), where R is a divalent aromatic radical having from 6–30 carbon atoms, $R^1$ is a monovalent organic radical selected from the class consisting of $C_{(1-8)}$ alkyl radicals and organic radicals having from 6–20 carbon atoms, selected from the class consisting of aromatic hydrocarbon radicals and halogenated derivatives thereof.

4. A method in accordance with claim 1, where R is 2,2-bis(4-phenyl)propylene.

5. A method in accordance with claim 1, where $R^1$ is methyl.

6. A method in accordance with claim 1, where the aromatic bis(ether phthalic acid) is 2,2-bis[4-(3,4-dicarboxyphenoxy)phenyl]propane.

7. A method in accordance with claim 1, where an organic carboxylic acid catalyst is used in the reaction mixture.

8. A method in accordance with claim 1, where an organic amine catalyst is used in the reaction mixture.

9. A method in accordance with claim 1, where water is introduced into the reaction mixture as a separate aqueous make-up feed to replace water vented as part of the vapor phase from the reaction mixture.

10. A method in accordance with claim 1, where the vapor phase is passed into a condensor to provide for the recovery of the N-organo-substituted phthalimide.

11. A method in accordance with claim 2, where the bis-anhydride is 2,2-bis[4-(3,4-dicarboxyphenoxy)phenyl]propane dianhydride.

12. A continuous method for making an aromatic bis(carbonyl) compound selected from the class consisting of a tetra-acid of the formula,

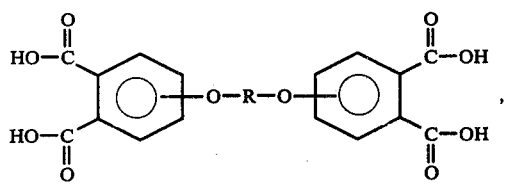

and a bisanhydride of the formula,

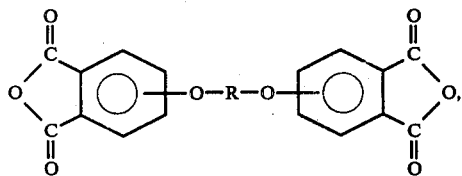

which comprises
(A) heating at a temperature of 100°-300° C. a mixture comprising by weight
(i) aromatic bis(ether phthalimide) of the formula,

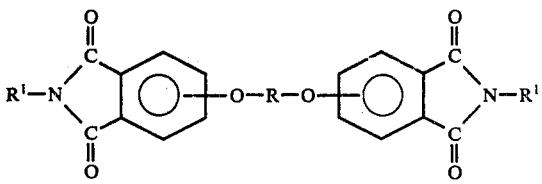

(ii) 0.01 to 100 parts of water per part of (i),
(iii) 0.3 to 20 parts of phthalic anhydride or phthalic acid per part of (i)

resulting in an exchange between phthalic acid or phthalic anhydride and aromatic bis(ether phthalimide) to produce a multiphase reaction mixture comprising the aromatic bis(dicarbonyl) compound in a liquid phase and an N-organo substituted phthalimide of the formula,

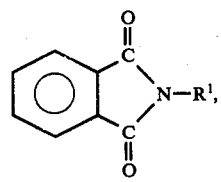

in the vapor phase
(B) continuously venting the vapor phase from the reaction mixture of (A) to provide for the selective removal of the N-organo substituted phthalimide,
(C) at least intermittently drawing off the bis(carbonyl) compound from the mixture of (A),
(D) continuously introducing the aromatic bis(ether phthalimide, the phthalic acid or phthalic anhydride and water into the mixture of (A),
(E) nitrating the N-methyl phthalimide separated in accordance with (B), and
(F) continuously forming the aromatic bis(ether phthalimide) by the displacement of said N-organo substituted phthalimide of (E) with an alkali phenoxide, where R is a divalent aromatic radical having from 6-30 carbon atoms, $R^1$ is a monovalent organo radical selected from the class consisting of $C_{(1-8)}$ alkyl radicals and organic radicals having from 6-20 carbon atoms, selected from the class consisting of aromatic hydrocarbon radicals and halogenated derivatives thereof.

* * * * *